United States Patent [19]

Bessman et al.

[11] Patent Number: 4,664,119
[45] Date of Patent: May 12, 1987

[54] TRANSCUTANEOUS GALVANIC ELECTRODE OXYGEN SENSOR

[75] Inventors: Samuel P. Bessman, Los Angeles; Lyell J. Thomas, Jr., San Pedro; Ennis C. Layne, San Gabriel, all of Calif.

[73] Assignee: University of Southern California, Los Angeles, Calif.

[21] Appl. No.: 805,070

[22] Filed: Dec. 4, 1985

[51] Int. Cl.$^4$ .............................................. A61B 5/00
[52] U.S. Cl. .................... 128/635; 204/403; 204/408; 204/415; 204/431
[58] Field of Search ............... 128/635; 204/403, 408, 204/414, 415, 431, 432

[56] References Cited

U.S. PATENT DOCUMENTS 3,528,904  9/1970  Cliffgard ............................ 204/408
3,929,588  12/1975  Parker et al. ..................... 204/415 X
4,495,051  1/1985  Fujita et al. ........................ 204/408

FOREIGN PATENT DOCUMENTS 2067764  7/1981  United Kingdom ............... 204/403

OTHER PUBLICATIONS

Baker, "A Galvanic Cell ... Man", Med. & Biol. Eng., vol. 13, No. 3, pp. 443-449, May 1975.

Primary Examiner—Lee S. Cohen
Attorney, Agent, or Firm—Nilsson, Robbins, Dalgarn, Berliner, Carson & Wurst

[57] ABSTRACT

A galvanic electrode oxygen sensor which is useful in measuring transcutaneous oxygen pressure (pO$_2$) contains a cathode in the form of a porous film of a metal below hydrogen in the Electromotive Series, an anode of a metal above hydrogen in the Electromotive Series, an electrolyte and an oxygen-permeable membrane in contact with the cathode and adapted to contact the skin of a patient. The sensor may also contain temperature measuring device or structure for compensating for temperature variations.

10 Claims, 5 Drawing Figures

TRANSCUTANEOUS GALVANIC ELECTRODE OXYGEN SENSOR

BACKGROUND OF THE INVENTION

1. Field of the Invention

This invention relates to oxygen sensors. In one of its more particular aspects, this invention relates to a galvanic electrode oxygen sensor for measuring transcutaneous oxygen pressure. In yet another of its more particular aspects, this invention relates to a temperature compensated oxygen sensor.

Electrodes for measuring transcutaneous $pO_2$ are useful in various clinical applications. For example, such electrodes can be used in surgery to monitor tissue oxygen during the course of anesthesia, to monitor shock in trauma situations in which there is blood loss or to monitor tissue oxygen pressure in newborn infants to detect respiratory or vascular problems.

2. Prior Art

A glucose-oxygen sensor in which an oxygen-sensitive primary cell consists of a silver cathode, a lead anode and an acidic buffered electrolyte in a flat plastic housing is disclosed in S. P. Bessman and R. D. Schultz, "Prototype Glucose-Oxygen Sensor for the Artificial Pancreas", *Trans. Amer. Soc. Artif. Int. Organs,* 19:361-364 (1973).

An oxygen-sensitive primary cell in which the cathode is made of thin silver wire tightly wound into a flat spiral with oxygen diffusing through a polypropylene membrane and then through the electrolyte between successive turns of the spiral is described in S. P. Bessman and R. D. Schultz, "Progress Toward a Glucose Sensor for the Artificial Pancreas", in *Ion Selective Microelectrodes,* H. J. Berman and N. C. Hebert, Eds., pp. 189-197, Plenum Publishing Corporation, New York (1974).

An oxygen electrode in which the skin is heated to maintain constant temperature of the electrode is disclosed in A. Huch, R. Huch, B. Arner and G. Booth, "Continuous Transcutaneous Oxygen Tension Measured with a Heated Electrode", *Scand. J. Clin. Lab. Invest.,* 31:269-275 (1973).

A probe for temperature compensated transcutaneous carbon dioxide measurement in which an error signal is generated by temperature sensor means is disclosed in U.S. Pat. No. 4,301,807 to R. A. Mentelos, Nov. 24, 1981.

An implantable glucose sensor having an electrical circuit for making corrections for temperature and oxygen concentration is disclosed in U.S. Pat. No. 4,431,004, to S. P. Bessman, E. C. Layne and L. J. Thomas, Feb. 14, 1984.

Although the above references relate to various techniques for measuring oxygen, glucose and carbon dioxide, none provides a convenient means for measuring $pO_2$ transcutaneously at ambient temperature with a conveniently manufactured sensor that may be disposable.

3. Objects

The principal object of the present invention is to provide a convenient means for measuring transcutaneous $pO_2$.

Another object of this invention is to provide such a means which does not require the heating of the skin of the patient whose $pO_2$ is being measured.

Another object of this invention is to provide a transcutaneous oxygen sensor which can be manufactured conveniently.

Another object of this invention is to provide a transcutaneous oxygen sensor which is disposable.

Other objectives and advantages of the present invention will become apparent in the followed detailed description.

SUMMARY OF THE INVENTION

The present invention provides a galvanic electrode oxygen sensor for measuring transcutaneous oxygen pressure ($pO_2$) which displays improved sensitivity over previously available devices, is more convenient to use than prior art sensors, is conveniently fabricated and is readily disposable.

The sensor of the present invention includes a cathode fabricated of a metal below hydrogen in the Electromotive Series, that is, a metal whose oxidation potential is negative with respect to hydrogen; an anode fabricated of a metal above hydrogen in the Electromotive Series; an electrolyte which provides a source of hydrogen atoms; and an oxygen-permeable membrane in contact with the cathode and adapted to contact the skin of a patient whose transcutaneous $pO_2$ is being measured. The cathode is fabricated in the form of a porous metal film capable of absorbing a layer of hydrogen atoms on its surface and adapted to ensure contact of transcutaneous oxygen at the interface between the cathode surface and the electrolyte. For this purpose a film of metal having pores sufficiently large to permit oxygen molecules to contact the electrolyte within the pores of the metal is utilized. Use of a porous metal film as the cathode of the sensor simplifies the fabrication of the sensor making its disposability feasible.

In a preferred embodiment, the electrode is provided with a temperature measuring device such as a thermistor and preferably with the circuitry necessary to give a read-out of $pO_2$ corrected for temperature.

DESCRIPTION OF THE PREFERRED EMBODIMENT

In a preferred embodiment, the present invention provides a means for measuring the transcutaneous oxygen pressure ($pO_2$) and correcting the value obtained for temperature fluctuations. The measurement of temperature can be separate from the sensor, but for reasons of convenience it is preferred that a temperature measuring device be included in the sensor. Since oxygen pressure determinations are very susceptible to temperature variation, it is essential that any measurement of $pO_2$ be corrected for temperature. This is particularly true where the value of $pO_2$ is very low, such as in the measurement of transcutaneous $pO_2$. Such correction can be accomplished manually, but it is preferred that a temperature compensating circuit, such as will be described below, be included in the sensor.

Figure 1:
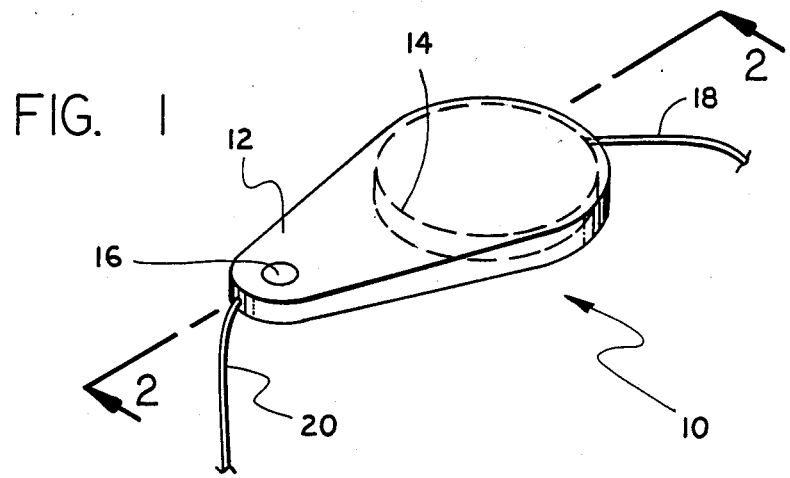
FIG. 1 is a diagrammatic perspective view of a sensor according to the present invention.

A sensor according to the present invention is shown in FIG. 1 wherein the numeral 10 represents the sensor. Such sensor consists of a plastic container 12 having an electrode well 14 and a thermistor 16. A wire lead 18 is connected to electrode well 14, as will be more particularly described below. A wire lead 20 is connected to thermistor 16.

Figure 2:
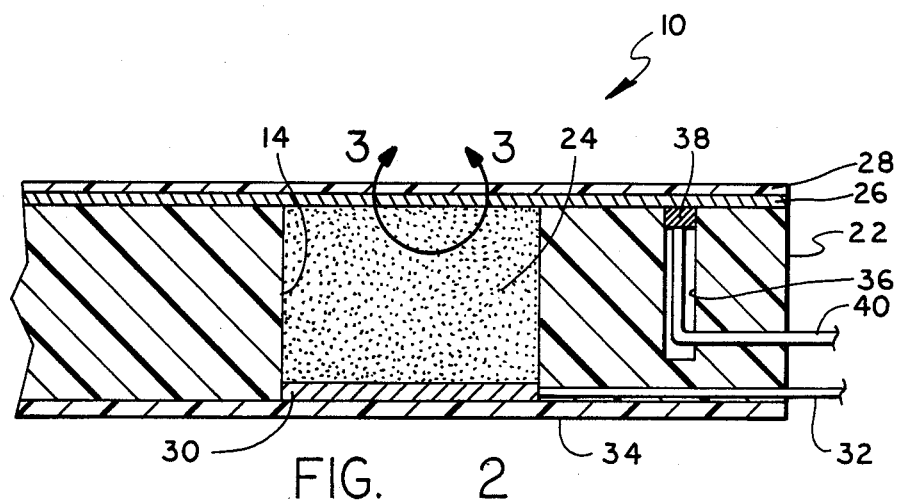
FIG. 2 is a diagrammatic cross-sectional view of the sensor taken along the line 2—2 of FIG. 1.

In FIG. 2, which is an enlarged view of a cross-section of a portion of sensor 10, there is shown the more detailed construction of the sensor of the present invention. Sensor 10 consists of a body 22 having therein electrode well 14 containing an electrolyte 24. At the top of well 14 there is a cathode 26. On top of the cathode is an oxygen-permeable membrane 28. At the bottom of electrode well 14 is an anode 30, to which is connected a wire lead 32. An impervious cap 34 closes the bottom of electrode well 14. Within body 22 there is a cavity 36 containing a conductor 38 which contacts cathode 26 and is connected to a wire lead 40.

Figure 3:
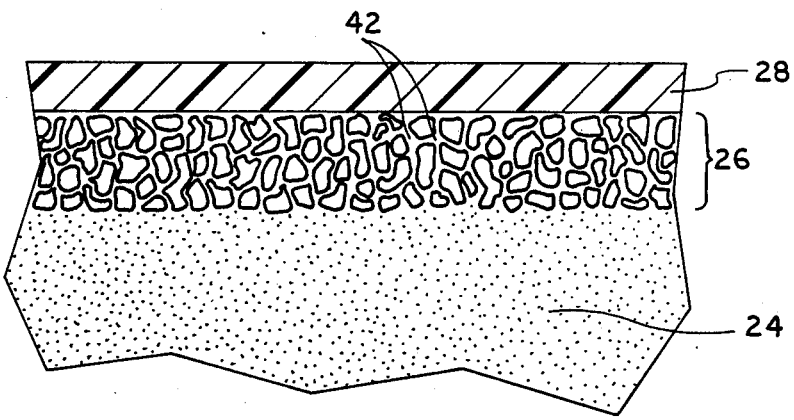
FIG. 3 is a greatly enlarged view of a portion of FIG. 2 generally taken along the line 3—3 of FIG. 2.

FIG. 3 is a microscopic view of the region 3—3 of FIG. 2, showing electrolyte 24, cathode 26 and oxygen-permeable membrane 28. It can be seen from FIG. 3 that cathode 26 contains a multiplicity of interstices 42 which permit oxygen which passes through membrane 28 to contact electrolyte 24.

The sensor of the present invention is a galvanic electrode oxygen sensor which functions by a depolarization mechanism. The dissimilar metal cathode and anode in an electrolyte constitutes an electromotive cell which produces current, polarizes itself by the adsorption of activated hydrogen atoms upon the cathode surface, and as a result, stops working when the cell has delivered a tiny amount of current. Oxygen, which passes through the oxygen-permeable membrane to contact the cathode of the electromotive cell, depolarizes the cell by reacting with the adsorbed hydrogen atoms and permits it to pass a current which is proportional to the amount of oxygen passing through the oxygen-permeable membrane and thence contacting the cathode.

The body of the sensor can be fabricated of any electrical insulating material, such as plastics. Such material may be a plastic which is nonpermeable to oxygen, such as an epoxy, or an oxygen-permeable plastic, such as TEFLON ™.

The oxygen-permeable membrane can be any oxygen-permeable plastic which is compatible with skin, for example, polypropylene or TEFLON ™. The membrane may, in appropriate cases, be integral with the sensor body, where the sensor body is fabricated of an electrical insulating material which is permeable to oxygen, such as TEFLON ™.

The cathode can be fabricated of any metal below hydrogen in the Electromotive Series, for example, silver, platinum or gold. Silver is especially preferred. Although a variety of metals may be used as the cathode in the sensor of the present invention, it is essential that the cathode be capable of adsorbing a layer of activated hydrogen atoms on its surface and that the cathode be porous so as to provide a metal-gas-electrolyte interface at which simultaneous contact of metal, gas and electrolyte can take place. For the latter purpose, the metal cathode must be perforated or spongy throughout its cross-section. A mossy platinum electrode is spongy at the surface, but contains a solid metallic substrate, and would therefore not be satisfactory for use in this invention. Suitable cathodes can be fabricated, for example, by evaporating or sputtering a porous metal film upon the oxygen-permeable membrane or body or by electrodepositing a porous metallic film thereon. Any porous film of a metal below hydrogen in the Electromotive Series can be used, provided that the pores in the film are large enough to permit the simultaneous contact of metal, gas and electrolyte, which is necessary for depolarization to occur. Gold leaf, for example, is not satisfactory for this purpose because it is not sufficiently porous to enable the desired depolarization reaction. However, a perforated film of gold leaf or other suitable metal foil can be used. A preferred cathode is a spongy metallic film which not only permits permeation by oxygen but is also permeable to the electrolyte, thus providing a large surface area at which metal, gas and electrolyte may contact one another simultaneously.

The anode can be any metal above hydrogen in the Electromotive Series, for example, lead, cadmium or tin. The form of anode is not critical, since the depolarization reaction necessary to permit current flow takes place at the cathode rather than at the anode. A metal film can be applied to the surface of the body of the sensor or the impervious cap, if desired. However, any form of metal anode is satisfactory. Furthermore, the anode, if in the form of a film, need not be applied so as to render it porous.

The electrolyte, which provides an internal connection or bridge between cathode and anode and which, in conjunction with the cathode and anode, forms an electromotive cell, can be any fluid which will provide a source of hydrogen atoms. In general, the electrolyte should have a pH in the range of pH 2–8 so as to not permit the formation of an impermeable precipitate upon the anode. Suitable materials include acetic acid, tartaric acid, citric acid, malic acid, oxalic acid and hydrochloric acid. Multibasic acids are preferred. The electrolyte may be a liquid or, more conveniently, a gel.

Conductor 38, which serves the function of connecting cathode 26 to an external circuit by means of wire lead 40, can be a gold or silver filled epoxy, which is readily adhered to both cathode 26 and wire lead 40 within cavity 36. Other means may be used for connecting the cathode to the external circuit, if desired. Anode 30 is connected to the external circuit by means of wire lead 32.

Because of the use of a metal film as cathode, resulting in ease of fabrication of the sensor and because of low material costs, it is feasible to dispose of the sensor following use. Thus, rather than having to sterilize the sensor for reuse, it is economical to simply discard the sensor.

The oxygen sensitivity of the sensor of this invention is better than that of previous sensors used for measuring transcutaneous oxygen pressure, particularly at low oxygen tensions where prior art sensors display less sensitivity than at higher values of $pO_2$. The present sensor is extremely sensitive at below about 10 millimeters Hg $pO_2$ and is somewhat more sensitive than prior art sensors at all levels of $pO_2$ encountered in the transcutaneous measurement of $pO_2$ in humans and other animals.

Figure 4:
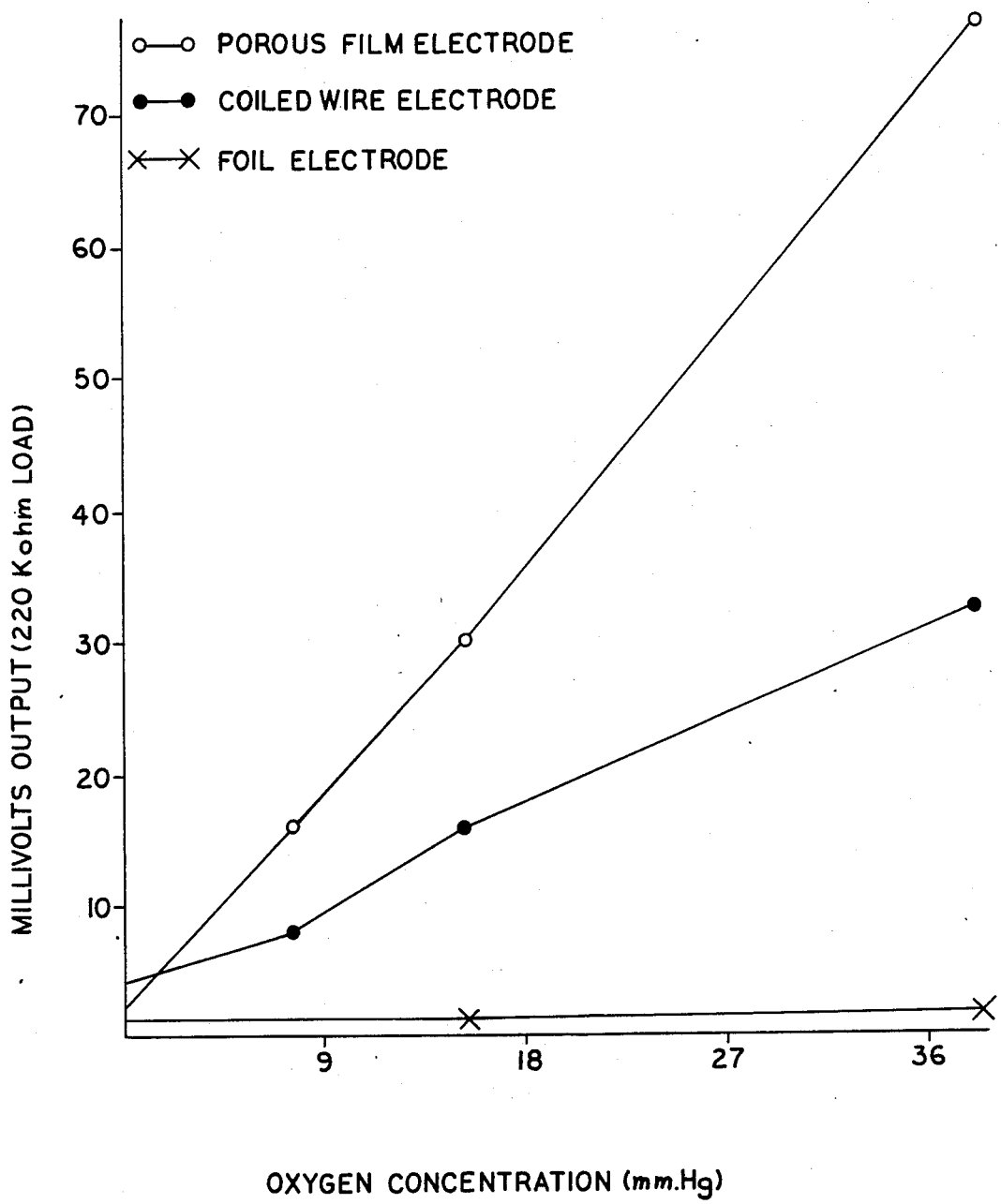
FIG. 4 is a series of curves showing the response of the sensor of the present invention compared to other types of sensors.

The comparative sensitivities of the sensor of the present invention and two prior art sensors are shown in FIG. 4. The upper curve shows the output potential at various oxygen concentrations for a sensor fabricated according to the present invention, consisting of a porous film of silver evaporated onto the inner side of a polypropylene membrane. The middle curve shows the response of a coiled wire electrode consisting of a coil of silver immersed in electrolyte and over which is fixed a polypropylene membrane. The bottom curve shows the response of a foil electrode consisting of a 5-mil silver foil, the lower side of which is in contact with the electrolyte and the outer dry side of which is covered by a polypropylene membrane.

It can be seen from these curves that the sensitivity of the sensor of this invention is significantly greater than that of the coiled wire electrode, in which oxygen reaches the electrode-electrolyte interface by passage between layers of the coil. It can also be seen that the sensitivity of the foil electrode, which is essentially impermeable to oxygen because of the thickness of the silver foil, is so low as to be of almost no use whatsoever.

It has been found convenient in utilizing the sensor of the present invention, to measure a potential indicative of the value of $pO_2$. Such measured potential must be corrected for temperature. The inclusion of a thermistor or other temperature measuring device in the sensor is a convenient means of reading the temperature near the site of measurement of the transcutaneous $pO_2$ and correcting the temperature sensitive $pO_2$ measurement to some standard reference condition, as will be further described below. Alternatively, if desired, temperature measurements can be accomplished apart from the measurement of transcutaneous oxygen pressure using the sensor of the present invention with a separate temperature measuring device. However, it is more convenient for the temperature measurement to be accomplished simultaneously with the measurement of $pO_2$ and as close to the measurement site as possible, since $pO_2$ measurements are extremely temperature sensitive. It is sometimes important, in addition, to have a reading of the temperature itself as an indication of the environment in which the $pO_2$ measurement is taken. Thus, it is sometimes desirable for the temperature measuring device to accomplish two functions simultaneously, namely, producing a reading of the temperature and providing an electrical signal which can be used to correct the $pO_2$ for temperature induced artifacts. It is, of course, possible to obtain a $pO_2$ correction for temperature without actually obtaining a reading of the temperature itself. However, in some instances, it is desirable to obtain the temperature reading as well as the corrected $pO_2$.

Figure 5:
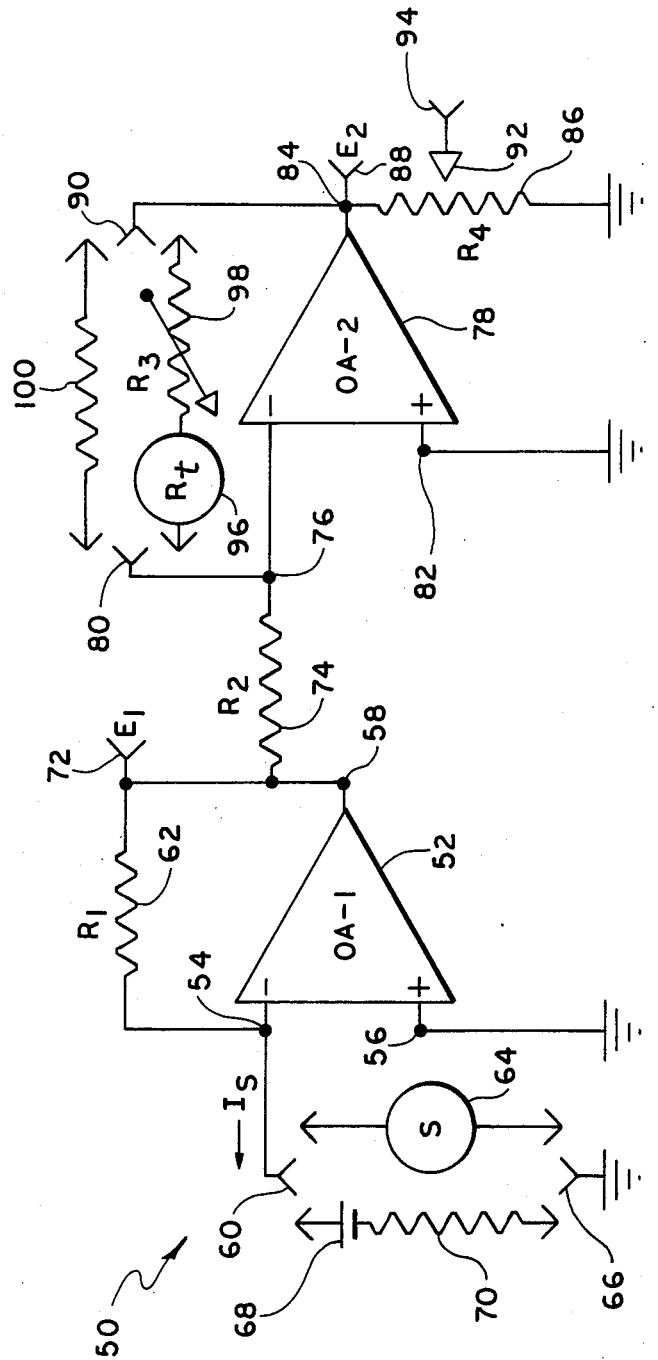
FIG. 5 is a circuit diagram of a temperature compensating circuit which can be used with the sensor of this invention.

Referring now to FIG. 5, the numeral 50 represents a temperature compensating circuit. An operational amplifier 52 having input terminals 54 and 56 and an output terminal 58, constitutes, together with its associated circuit elements, a current to voltage converter. Terminal 56 of operational amplifier 52 is grounded. Terminal 54 is connected to sensor terminal 60 and resistor 62. Oxygen sensor 64 can be connected beteween sensor terminal 60 and sensor terminal 66, which is grounded. Alternatively, there may be connected between sensor terminals 60 and 66 a battery 68 and resistor 70 in series. Output terminal 58 is connected to uncompensated output potential terminal 72 and, through resistor 74 to input terminal 76 of operational amplifier 78, which is also connected to thermistor terminal 80. The other input terminal 82 of operational amplifier 78 is grounded. Output terminal 84 of operational amplifier 78 is connected through variable resistor 86 to ground. Output terminal 84 is also connected to temperature compensated output potential terminal 88 and to thermistor terminal 90. Contact 92 of variable resistor 86 is connected to output potential terminal 94. Thermistor 96 and variable resistor 98 in series connection are adapted for connection between thermistor terminals 80 and 90. Alternatively, resistor 100 can be connected between thermistor terminals 80 and 90.

The analog circuit described employs a thermistor to provide temperature compensation for a galvanic electrode oxygen sensor, making it unnecessary to heat the skin where it contacts the sensor in order to obtain a reliable oxygen tension measurement. Thermistors in general have a negative temperature coefficient, while galvanic electrode oxygen sensors have a positive temperature coefficient, resulting in a 3-5 percent increase in current output for each degree Centigrade increase in temperature at a constant oxygen tension. Connecting a thermistor across the galvanic electrode oxygen sensor may therefore suffice to provide temperature compensation. However, the circuit described above provides better temperature compensation, as will be described below. In addition, other temperature compensating curcuits may be used.

The first operational amplifier (OA-1) is configured as a current to voltage converter. This circuit is an "ideal ammeter" since it requires no shunting resistance across the current source. With the oxygen sensor, S, connected between sensor terminals 60 and 66, the current output of the oxygen sensor IS is converted by OA-1 to a voltage $E_1$ proportional to this current as follows. Since no significant current flows into either input terminal (+ or −) of an operational amplifier, all of $I_S$ flows from the output terminal of OA-1 through $R_1$, causing a voltage $E_1$ compared to ground to appear at the output terminal of OA-1 as given by $E_1 = I_S \times R_1$.

The second operational amplifier (OA-2) modifies the output of OA-1 to give another voltage, $E_2$ which is proportional to sensor current but compensated for temperature. OA-2 contains in its feedback loop connected between thermistor terminals 80 and 90 the thermistor $R_t$ plus a passive variable resistor $R_3$. The equation for OA-2 is derived as follows. The current through $R_2$ and through $R_t + R_3$ must be the same. Thus $E_1/R_2 = E_2/[R_t + R_3]$. Rearrangement of the terms gives the amplification factor for OA-2 as $E_2/E_1 = [R_t + R_3]/R_2$. From this, it can be seen that the function of $R_3$ is to reduce the effect of the thermistor in the feedback loop. If $R_3 = 0$, the effect of the thermistor is maximum, but if $R_3$ is large, the effect of the thermistor is nil. $E_2$ is made proportional to the temperature corrected oxygen sensor current by choosing $R_3$ so that $E_2$ is the same when the sensor is exposed to any two different temperatures within the operating range (e.g., 25 and 35 degrees Centigrade) at the same oxygen tension. The reduction (or increase) in gain of OA-2 resulting from the change in resistance of $R_t + R_3$ then exactly matches the change in $E_1$ resulting from the effect of temperature on the oxygen sensor. $E_2$ then remains constant regardless of temperature at a given oxygen tension. By adjusting the voltage divider $R_4$, these voltage readings can be made to give numerical values corresponding directly to oxygen sensor current. In order to measure the uncompensated output from the sensor, a 2200 ohm passive resistor 100 (the resistance of the thermistor at 25 degrees Centigrade) is substituted in place of the thermistor in the feedback loop of OA-2.

To calibrate the system, a current standard consisting of a 1.5 v silver oxide "button cell" 68 in series with a 10 megohm resistor 70 may be plugged into the oxygen sensor terminals 60 and 66.

Typical active components for a prototype include the following: Type 441 IC Operational Amplifier (National Semiconductor Corp., Santa Clara, Calif.); and Type YSI 44004 thermistor (Yellow Springs Instrument Co., Yellow Springs, Ohio).

The foregoing description of the invention has been directed to particular preferred embodiments for purposes of explanation and illustration. It will be apparent, however, to those skilled in the art that many modifications and changes in the particular design of the sensor and the materials used therein as well as in the method of use may be made without departure from the scope and spirit of the invention. It is applicants' intention in the following claims to cover all such equivalent modifications and changes as fall within the true spirit and scope of the invention.

What is claimed is:

1. A galvanic electrode oxygen sensor for the measurement of transcutaneous $pO_2$ comprising:
    a cathode fabricated of a metal below hydrogen in the Electromotive Series;
    an anode fabricated of a metal above hydrogen in the Electromotive Series;
    an electrolyte contacting said cathode and anode; and
    an oxygen permeable membrane fabricated of a plastic material which is compatible with skin in contact with said cathode and adapted to contact the skin of a patient whose transcutaneous $pO_2$ is being measured;
    said cathode being in the form of a spongy metallic film permeable to oxygen and permeable to electrolyte adapted to provide a large surface area and to insure simultaneous contact of transcutaneous oxygen with the cathode surface and with said electrolyte.

2. A sensor according to claim 1 wherein said cathode is fabricated of a metal selected from the group consisting of silver, platinum and gold.

3. A sensor according to claim 1 wherein said cathode is a metal film deposited by evaporation.

4. A sensor according to claim 1 wherein said cathode is a metal film deposited by sputtering.

5. A sensor according to claim 1 wherein said cathode is a perforated metal foil.

6. A sensor according to claim 1 wherein said cathode is an electrodeposited metal film.

7. A sensor according to claim 1 wherein said anode is a fabricated of a metal selected from the group consisting of lead, cadmium and tin.

8. A sensor according to claim 1 which additionally comprises means for measuring the temperature of the skin simultaneously with the measurement of transcutaneous $pO_2$.

9. A sensor according to claim 8 wherein said means for measuring the temperature of the skin is a thermistor.

10. A sensor according to claim 1 which additionally comprises means, connected to the output of a current producing electromotive cell constituted by said cathode and said anode in contact with said electrolyte, for correcting said measurement of transcutaneous $pO_2$ for variations in temperature.

* * * * *